(12) United States Patent
Nagatsuka

(10) Patent No.: US 10,966,674 B2
(45) Date of Patent: Apr. 6, 2021

(54) RADIOGRAPHIC IMAGE DISPLAY APPARATUS, RADIOGRAPHIC IMAGING SYSTEM, AND DIAGNOSTIC METHOD

(71) Applicant: KONICA MINOLTA, INC., Tokyo (JP)

(72) Inventor: Sumiya Nagatsuka, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 108 days.

(21) Appl. No.: 16/287,912

(22) Filed: Feb. 27, 2019

(65) Prior Publication Data

US 2019/0298287 A1 Oct. 3, 2019

(30) Foreign Application Priority Data

Apr. 3, 2018 (JP) .............................. JP2018-071246

(51) Int. Cl.
*A61B 6/00* (2006.01)
*G16H 30/20* (2018.01)
*G16H 30/40* (2018.01)
*G06T 7/00* (2017.01)

(52) U.S. Cl.
CPC .............. *A61B 6/463* (2013.01); *A61B 6/486* (2013.01); *A61B 6/5205* (2013.01); *G06T 7/0012* (2013.01); *G16H 30/20* (2018.01); *G16H 30/40* (2018.01); *G06T 2207/10116* (2013.01); *G06T 2207/30012* (2013.01)

(58) Field of Classification Search
CPC ....... A61B 6/463; A61B 6/486; A61B 6/5205; G06T 7/0012; G06T 2207/10116; G06T 2207/30012; G16H 30/20; G16H 30/40; G16H 50/20
See application file for complete search history.

(56) References Cited

U.S. PATENT DOCUMENTS

| 7,155,042 | B1* | 12/2006 | Cowan | A61B 5/055 |
| | | | | 382/128 |
| 7,230,262 | B2 | 6/2007 | Sendai | |
| 10,278,661 | B2* | 5/2019 | Muraoka | G16H 30/40 |
| 2003/0055331 | A1* | 3/2003 | Kotmel | A61B 6/541 |
| | | | | 600/410 |

(Continued)

FOREIGN PATENT DOCUMENTS

| JP | 2005342088 A | 12/2005 |
| JP | 2015084821 A | 5/2015 |
| JP | 2015223233 A | 12/2015 |

*Primary Examiner* — Mark R Gaworecki
(74) *Attorney, Agent, or Firm* — Holtz, Holtz & Volek PC

(57) ABSTRACT

A radiographic image display apparatus 3 included in a radiographic imaging system 100 includes a hardware processor that obtains an image data item on each of the frame images generated by the radiographic imaging apparatus 2, detects a situation of the subject at least at a time point in the dynamic imaging, associates the detected situation of the subject with the obtained image data items, and issues a specific output for notification that the subject is in a specific situation when the subject is in a state of a specific frame image fs, in a case where the display is caused to display the specific frame image fs, this specific frame image fs being taken when it is detected that the situation of the subject is the specific situation.

13 Claims, 4 Drawing Sheets

(56) References Cited

U.S. PATENT DOCUMENTS

| | | | | |
|---|---|---|---|---|
| 2005/0263730 | A1* | 12/2005 | Sendai | G03B 42/08 |
| | | | | 250/583 |
| 2015/0073257 | A1* | 3/2015 | Muraoka | A61B 6/54 |
| | | | | 600/407 |
| 2017/0020469 | A1* | 1/2017 | Lee | A61B 6/463 |
| 2017/0020470 | A1* | 1/2017 | Tezuka | A61B 6/542 |
| 2017/0087416 | A1* | 3/2017 | Hu | G06K 9/00348 |
| 2017/0140127 | A1* | 5/2017 | Schulhauser | G06F 19/321 |
| 2017/0360392 | A1* | 12/2017 | Kaneko | A61B 6/486 |

\* cited by examiner

| FRAME NO. | 1 | 2 | 3 | 4 | 5 | 6 | 7 | 8 | 9 | 10 | 11 | 12 | 13 | 14 | 15 | .. |
|---|---|---|---|---|---|---|---|---|---|---|---|---|---|---|---|---|
| SENSING LEVEL OF SUBJECT | 0 | 0 | 0 | 0 | 0 | 0 | 0 | 1 | 5 | 2 | 0 | 0 | 0 | 0 | 0 | .. |
| DETECTION LEVEL OF SITUATION DETECTOR | 0 | 0 | 0 | 0 | 0 | 0 | 0 | 0 | 1 | 5 | 2 | 0 | 0 | 0 | 0 | .. |

RADIOGRAPHIC IMAGE DISPLAY APPARATUS, RADIOGRAPHIC IMAGING SYSTEM, AND DIAGNOSTIC METHOD

BACKGROUND

Technological Field

The present invention relates to a radiographic image display apparatus, a radiographic imaging system, and a diagnostic method.

Description of the Related Art

As for a radiographic imaging system of performing dynamic imaging that repetitively generates frame images of a subject, during diagnosis using taken dynamic images, in order to facilitate diagnosis or achieve more detailed diagnosis (perform diagnosis support), techniques described in the following documents have been proposed.

For example, Japanese Patent Laid-open No. 2015-084821 describes a diagnosis support information generation method that includes: imaging means for generating a plurality of frame images through dynamic imaging; a load application step of applying a predetermined load; an imaging step of performing first imaging that takes dynamics of a subject site by the imaging means immediately after application of the predetermined load to the subject site, and of performing second imaging that takes dynamics of the subject site by the imaging means after a predefined time period has elapsed since the first imaging; and a diagnosis support information generation step of generating diagnosis support information on the basis of a change between a first characteristic amount and a second characteristic amount.

Japanese Patent Laid-open No. 2015-223233 describes a contrast medium injection support apparatus that includes a receiver which receives an imaging start time of an X-ray contrast image; a determiner that determines an contrast agent injection start time; and a notifier that preliminarily notifies an imaging operator about start of injecting the contrast agent.

Japanese Patent Laid-open No. 2005-342088 describes a radiographic image taking apparatus that images an object at a normal radiation dose when the phase detected by phase detection means becomes a desired phase.

The greatest object of dynamic imaging is to identify the cause of failures (pains and sufferings) occurring in a subject during the subject's various operations, by observing the movement of an imaging object site. To achieve this object, information related to a failure is necessary during reading dynamic images; the information indicates what failure occurs in what state of the imaging object site.

However, such information related to a failure does not given to a reading operator on the basis of the dynamic images obtained using any of the conventional diagnosis support techniques described in the above documents. Consequently, it has been difficult for the reading operator to identify the cause of the failure.

SUMMARY

The present invention has an object to allow easily and correctly reading the timing when the subject comes into a specific situation from the taken dynamic images, in a radiographic imaging system of performing dynamic imaging that repetitively generates frame images of the subject.

To achieve at least one of the abovementioned objects, according to a first aspect of the present invention, a radiographic image display apparatus reflecting one aspect of the present invention comprises a hardware processor that:

obtains an image data item on each of frame images by performing dynamic imaging that repetitively generates a frame image of a subject, the frame images being generated by a radiographic imaging apparatus;

causes a display to display the frame images based on the obtained image data items;

detects a situation of the subject at least at a time point in the dynamic imaging;

associates the detected situation of the subject with the obtained image data items; and issues a specific output for notification that the subject is in a specific situation when the subject is in a state of a specific frame image, in a case where the display is caused to display the specific frame image, the specific frame image being taken when it is detected that the situation of the subject is the specific situation.

According to a second aspect of the present invention, a diagnostic method reflecting one aspect of the present invention comprises dynamically imaging a joint or a cervical spine of a subject reciprocatively moving at a certain cycle, using a radiation irradiation apparatus that repetitively generates pulse radiation at a predetermined cycle, and a radiographic imaging apparatus that repetitively generates image data on a frame image according to the received radiation at a predetermined cycle;

transmitting image data items on obtained frame images to a radiographic image display apparatus that comprises a hardware processor that obtains an image data item on each of frame images generated by the radiographic imaging apparatus, causes a display to display the frame images based on the obtained image data items, detects a situation of the subject at least at a time point in the dynamic imaging, associates the detected situation of the subject with the obtained image data items, and issues a specific output for notification that the subject is in a specific situation when the subject is in a state of a specific frame image, in a case where the display is caused to display the specific frame image, the specific frame image being taken when the subject is detected to be in the specific situation; and reading the specific frame image displayed by the display.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiment of the present invention will be described with reference to the drawings. However, the scope of the invention is not limited to the disclosed embodiments.

[Radiographic Imaging System]

Figure 1:
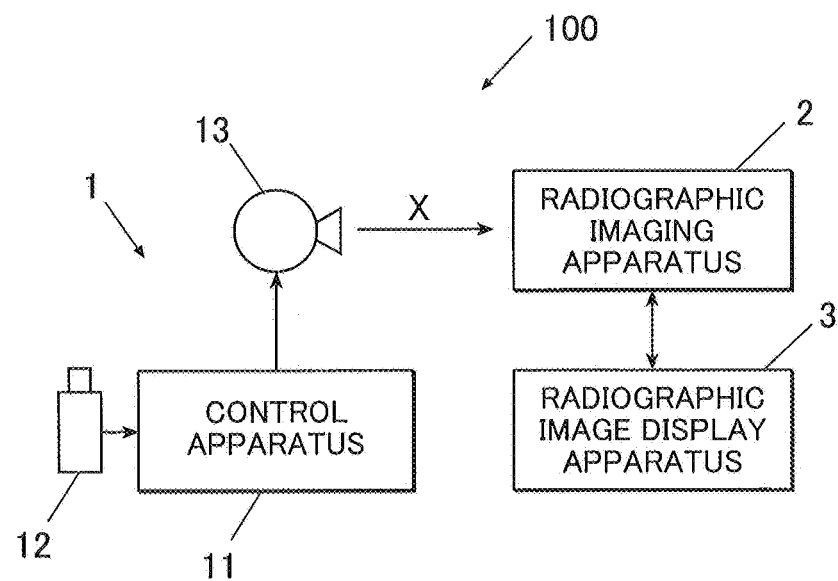
FIG. 1 is a block diagram showing a schematic configuration of a radiographic imaging system according to an embodiment of the present invention.

First, the configuration of a radiographic imaging system according to this embodiment (hereinafter an imaging system 100) is described. FIG. 1 is a block diagram showing a schematic configuration of the imaging system 100.

As shown in FIG. 1, the imaging system 100 of this embodiment includes a radiation irradiation apparatus (hereinafter an irradiation apparatus 1), a radiographic imaging apparatus (hereinafter an imaging apparatus 2), and a radiographic image display apparatus (hereinafter a display apparatus 3).

The irradiation apparatus 1 includes a control apparatus 11, an exposure switch 12, and a radiation source (tube) 13.

The control apparatus 11 is configured to allow application of a voltage according to a preset radiation exposure condition (a tube voltage, a tube current, an irradiation time period (mAs value), etc.) to the radiation source 13, on the basis of an event that the exposure switch 12 is pressed.

The radiation source 13 includes a rotating anode, a filament or the like, which is not shown. When the voltage is applied by the control apparatus 11, the filament emits an electron beam according to the applied voltage toward the rotating anode, and this rotating anode generates radiation (X-ray or the like) having a radiation dose according to the intensity of the electron beam.

Furthermore, the irradiation apparatus 1 is configured to allow pulse radiation having a predetermined time width to be repetitively emitted at a predetermined cycle, on the basis of one imaging operation (pressing of the exposure switch 12).

The irradiation apparatus 1 can change the direction of a radiation irradiation port of the radiation source 13, and can irradiate a subject at an upright position and the subject at a supine position with radiation (perform both upright position imaging and supine position imaging).

The irradiation apparatus 1 may be of a fixed type installed in an imaging room or a movable type provided with wheels.

The imaging apparatus 2 is configured to allow repetitively generating image data on a radiographic image based on the radiation received from the irradiation apparatus 1 at a predetermined cycle, and is connected to the display apparatus 3 wiredly or wirelessly in a communicable manner A specific configuration of the imaging apparatus 2 is described later.

The display apparatus 3 may be a PC, a mobile terminal or a dedicated apparatus, and is connected to the imaging apparatus 2 wiredly or wirelessly in a communicable manner. The details of the display apparatus 3 are also described later.

The imaging system 100 of this embodiment having such a configuration causes the irradiation apparatus 1 to irradiate a subject disposed between the irradiation apparatus 1 and the imaging apparatus 2 with radiation, thereby allowing radiation imaging of the subject.

In particular, the irradiation apparatus 1 repetitively irradiates the subject with pulse radiation, and the imaging apparatus 2 repetitively generates radiographic images of the subject, thereby allowing the dynamic images of the subject to be taken. Hereinafter, taking of the dynamic image is called "dynamic imaging," and each of the radiographic images constituting the dynamic image is called "frame image."

A console and an analysis device, which are not shown, can be incorporated in the imaging system 100. In this case, the console and the analysis device can be used as the display apparatus 3.

The imaging system 100 can also be used with connection to a Radiology Information System (RIS), a Picture Archiving and Communication System (PACS) or the like, which is not shown.

[Configuration of Radiographic Imaging Apparatus]

Figure 2:
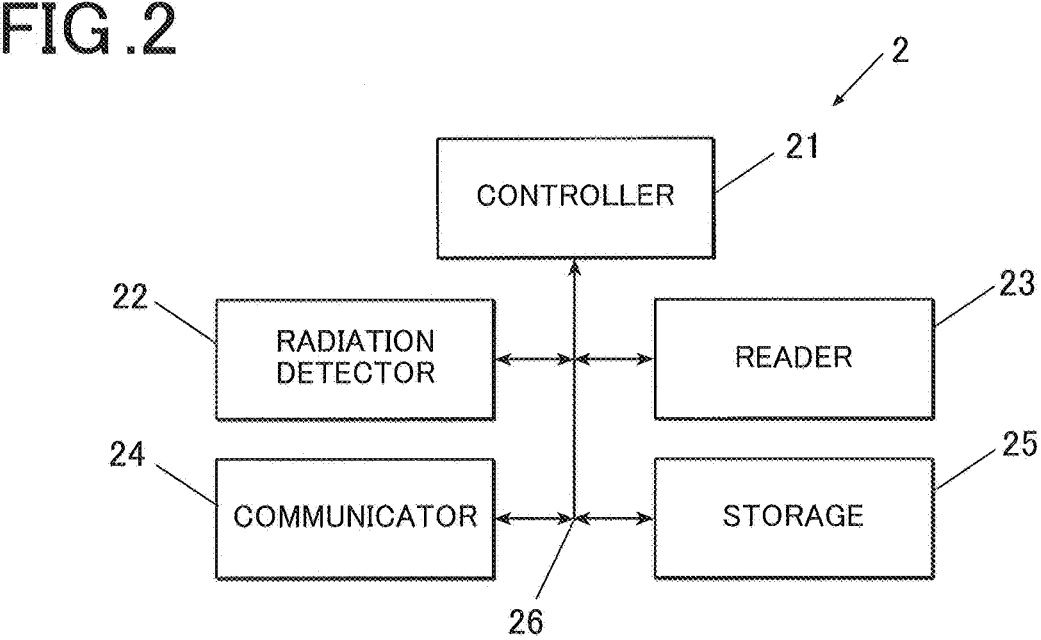
FIG. 2 is a block diagram showing a specific configuration of a radiographic imaging apparatus included in the radiographic imaging system in FIG. 1.

Next, the specific configuration of the imaging apparatus 2 included in the imaging system 100 is described. FIG. 2 is a block diagram showing the specific configuration of the imaging apparatus 2.

As shown in FIG. 2, the imaging apparatus 2 according to this embodiment includes a controller 21, a radiation detector 22, a reader 23, a communicator 24, a storage 25, and a bus 26 that connects these components.

The controller 21 includes a CPU (Central Processing Unit) and an RAM (Random Access Memory). The CPU of the controller 21 reads various programs stored in the storage 25 and deploys the programs in the RAM, executes various processes according to the deployed programs, and controls the operation of each component of the imaging apparatus 2 in a centralized manner.

AS the radiation detector 22, any radiation detector may be used as long as it includes a substrate on which pixels are two-dimensionally arranged, the pixels each including a radiation detection element that directly or indirectly generates an amount of charges according to the radiation dose of radiation by receiving the radiation from the outside, and a switch element that is provided between the corresponding radiation detection element and wiring and is switchable between an on state capable of energization between the radiation detection element and the wiring and an off state incapable of energization. A conventionally, publicly known one can be used.

That is, the imaging apparatus 2 may be of an indirect type that includes a scintillator and detects light emitted by the scintillator having received radiation, or of a direct type that directly detects the radiation without intervention of a scintillator or the like.

The reader 23 may be configured to be capable of reading, as a signal value, the amount of charges accumulated in each of the radiation detection elements and of generating image data on a radiographic image on the basis of each signal value. A conventionally, publicly known one can be used.

The communicator 24 may include a wireless module, and can transmit various pieces of information (signals and data) to another connected apparatus (the display apparatus 3 or the like) via a communication network, such as a LAN (Local Area Network) a WAN (Wide Area Network) or the Internet.

The storage 25 may include an HDD (Hard Disk Drive) or a semiconductor memory, and store various processing programs including various image processing programs, and parameters and files that are required to execute the programs.

The controller 21 of the imaging apparatus 2 having such a configuration has the following functions through the programs stored in the storage 25.

For example, the controller 21 has a function of repetitively switching the state of the imaging apparatus 2 sequentially to "initialization state," "accumulation state" and "reading and transfer state" at a predetermined cycle.

The "initialization state" is a state where an on voltage is applied to each switch element, and charges caused by the radiation detection element are not accumulated in each pixel (the charges are released to a signal line).

The "accumulation state" is a state where an off voltage is applied to each switch element, and the charges generated by the radiation detection element can be accumulated in each pixel (the charges are not released to the signal line).

The "reading and transfer state" is a state where the on voltage is applied to each switch element, the reader 23 is driven, and a signal value based on the charges having flown can be read.

The controller 21 also has a function of transmitting a pulse signal to the display apparatus 3 at timing of generating image data, for performing the dynamic imaging.

In dynamic imaging, the image data is repetitively generated at a predetermined cycle. Accordingly, the pulse signal is repetitively transmitted at the predetermined cycle.

[Radiographic Image Display Apparatus]

Figures 3, 4:
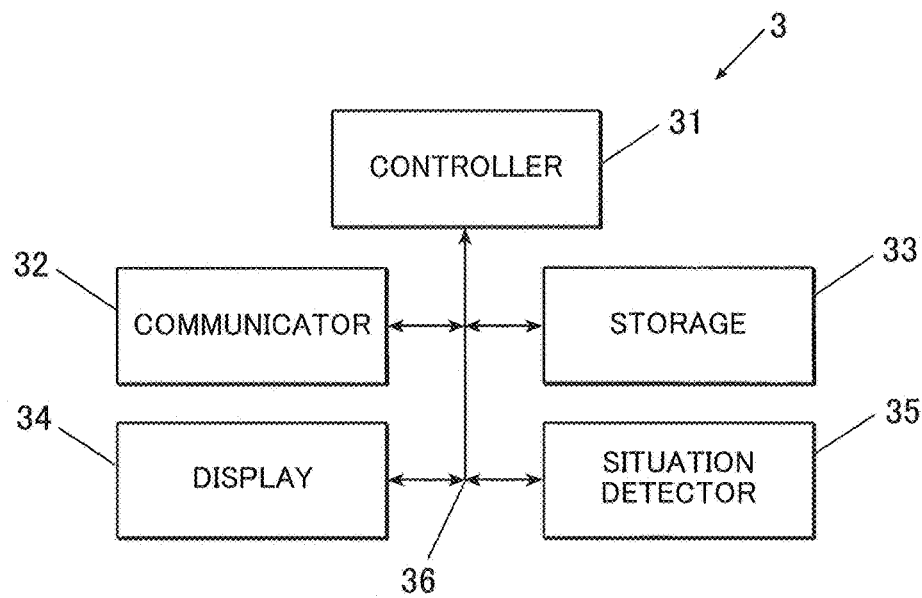
FIG. 3 is a block diagram showing a specific configuration of a radiographic image display apparatus included in the radiographic imaging system in FIG. 1.
FIG. 4 illustrates the difference between occurrence timing and detection timing of a specific situation.

Next, the details of the display apparatus 3 included in the imaging system 100 are described. FIG. 3 is a block diagram showing the specific configuration of the display apparatus 3.

As shown in FIG. 3, the display apparatus 3 includes a controller 31, a communicator 32, a storage 33, a display 34, a situation detector 35, and a bus 36 that connects these components.

The controller 31 includes a CPU (Central Processing Unit) and an RAM (Random Access Memory). The CPU of the controller 31 reads various programs stored in the storage 33 and deploys the programs in the RAM, executes various processes according to the deployed programs, and controls the operation of each component of the display apparatus 3 in a centralized manner.

The communicator 32 may include a wireless module, and can transmit various pieces of information (signals and data) to another connected apparatus (the imaging apparatus 2 or the like) via the communication network, such as a LAN (Local Area Network), a WAN (Wide Area Network) or the Internet.

The storage 33 may be a nonvolatile semiconductor memory, a hard disk or the like, and stores various programs to be executed by the controller 31 (including a program for performing an imaging control process described later), and parameters required for the programs to execute processes.

The display 34 may be a monitor, such as an LCD (Liquid Crystal Display) or a CRT (Cathode Ray Tube), and displays images, various pieces of information and the like according to an instruction of a display signal input from the controller 31.

The situation detector 35 is configured to be capable of accepting an input from the subject.

The situation detector 35 may have a configuration including the following components, for example.
  a microphone for collecting a speech output by the subject
  a push button that can be pushed by the subject
  a camera that images the expression of the face and the motion of the body of the subject FIG. 3 shows, as an example, the case where the situation detector 35 is connected to the controller 31 by the bus 36 (the situation detector has an integrated configuration). Since the situation detector 35 is required to be disposed adjacent to the subject during imaging, the situation detector 35 may be provided separately from the main body of the display apparatus 3, and an accepted input may be transmitted wiredly or wirelessly to the main body of the display apparatus 3.

The controller 31 of the display apparatus 3 having such a configuration has the following functions through the programs stored in the storage 33.

For example, the controller 31 has a function of receiving, through the communicator 32, image data on a radiographic image generated by the imaging apparatus 2 performing the radiation imaging.

When the dynamic imaging is performed, an image data item on each of multiple frame images generated by the imaging apparatus 2 is obtained.

The controller 31 also has a function of causing the display 34 to display a radiographic image based on the obtained image data.

When image data items on multiple frame images are received, the frame images are consecutively displayed as dynamic images on the display 34, or only a specific frame image is displayed as a still image.

The controller 31 has a function of detecting the state of the subject at least at one time point during dynamic imaging. In particular, this function includes detecting the specific situation according to a specific input to the situation detector 35 by the subject in a specific situation.

Here, the "specific situation" indicates a situation where the subject feels a failure (pains, sufferings and the like).

Specific methods of detecting the specific situation include, for example, the following methods.
  collecting a voice output by the subject through a microphone disposed adjacent to the subject.
  monitoring whether the push button held by the subject is pushed or not.
  analyzing an image taken by a camera for imaging the subject, and monitoring whether a significant change in expression or attitude appears or not.

The situation detector 35 may be configured to be capable of detecting the loudness of the voice, the strength of pressing the button, the degree of change in expression and attitude and the like, and further to monitor continuously the state of the subject over the period of dynamic imaging to be capable of detecting the change in degrees of pains and sufferings. In this case, the loudest voice, an output signal of the push button being pressed most strongly, the distortions of expression and attitude each serve as "specific input." A situation of the subject at a time point when the voice or the distortion of expression becomes largest and a time point when the button is pressed most strongly serve as the specific situation.

Instead of images taken by the camera, obtained dynamic images may be analyzed, and the specific situation may then be detected on the basis of the result of the analysis. In this case, the display apparatus 3 does not require the situation detector 35.

The accuracy of detecting the specific situation can be improved by combining two or more of the three detection methods described above.

The controller 31 further has a function of associating the detected situation of the subject with the obtained image data items.

Specifically, the number of pulse signals repetitively transmitted from the imaging apparatus 2 is counted. As described above, the pulse signal is transmitted every time the frame image is generated. Consequently, the count number serves as the frame number.

The count number of pulse signals (frame number) at the time point of the specific input to the situation detector 35 is associated with the fact that the specific input has been made.

Accordingly, at least a specific frame image fs taken when the specific situation is detected can be identified from among the frame images.

In the case where the strength of the input from the situation detector 35 is also detected, when the pulse signal is received from the imaging apparatus 2, the loudness of the voice, the strength of pushing the push button, the amount of distortion of expression and attitude and the like, which have been input into the situation detector 35, are converted into numerical values, for example, and the numerical values are associated with the count number of the received pulse signal (frame number). In this case, the frame image associated with the maximum numerical value is the specific frame image fs taken in the specific situation.

Besides, it is considered that a delay occurs from occurrence of the specific situation for the subject to input to the situation detector 35. That is, it can be considered that an error occurs between the timing when the specific situation actually occurs and the timing when the controller 31 detects the specific situation.

Specifically, as shown in FIG. 4, for example, even with the actual strongest pain during taking the ninth frame image (with the highest sensing level), the specific input to the situation detector 35 sometimes delays to the time of the 10-th frame imaging (delays by one frame).

Accordingly, the timing when the subject is detected to be in the specific situation may be corrected so as to approach the timing when the subject actually comes into the specific situation to thus reduce the error, by the following method, for example.

(Correction by Table)

A table representing the relationship between the attribute of at least one of the age and gender, and the average amount of delay (the number of frames) from occurrence of the specific situation to the specific input, is stored in the storage 33.

When the frame image is associated with the input to the situation detector 35 during imaging, the amount of delay corresponding to preliminarily input subject information is retrieved from the table, and the fact that the specific input has been made or the numerical value is delayed by the amount of delay and is associated with the frame image.

For example, in a case where the fact that the average amount of delay of women of 60 years old is one frame is stored in the table, the frame number at the time of the specific input is reduced by one and is associated, for dynamic imaging of a woman of 60 years old.

(Correction by Preliminarily Measured Value)

When a person senses a pain, he/she sometimes reflexively moves (outputs a voice, slightly moves or the like). Such timing of occurrence of the motion is considered to be infinitely close to the timing of occurrence of a pain. Accordingly, the controller 31 is configured to have a function of detecting the reflexive motion by the subject feeling a pain. Such detection of the reflexive motion may be made using the situation detector 35 (what is other than the push button is preferable) or using a dedicated device provided separately from the situation detector 35.

Before actual imaging, the subject rehearses for a practice of moving the body (for example, bending the neck forward and rearward, bending and stretching and rotating the knees), and a time period from detection of the reflexive motion by the subject feeling the pain to an input to the situation detector 35 is measured. The time period may be measured at the time of actual imaging.

When the frame image is associated with the input to the situation detector 35 during imaging, the fact that the specific input has been made or the numerical value is delayed by the measured time period and is associated with the frame image.

The controller 31 further has a function of issuing a specific output for notification that the subject is in the specific situation when the subject is in the state of the specific frame image fs, in a case where the display 34 is caused to display the specific frame image fs taken when detecting that the situation of the subject is the specific situation.

The specific output may be as follows.

Diagnosis support information based on the detected specific situation is generated, and the diagnosis support information is output together with the specific frame image fs.

The specific frame image fs is statically displayed.

(Display with Diagnosis Support Information)

Specific diagnosis support information may be as follows.

Figure 5:
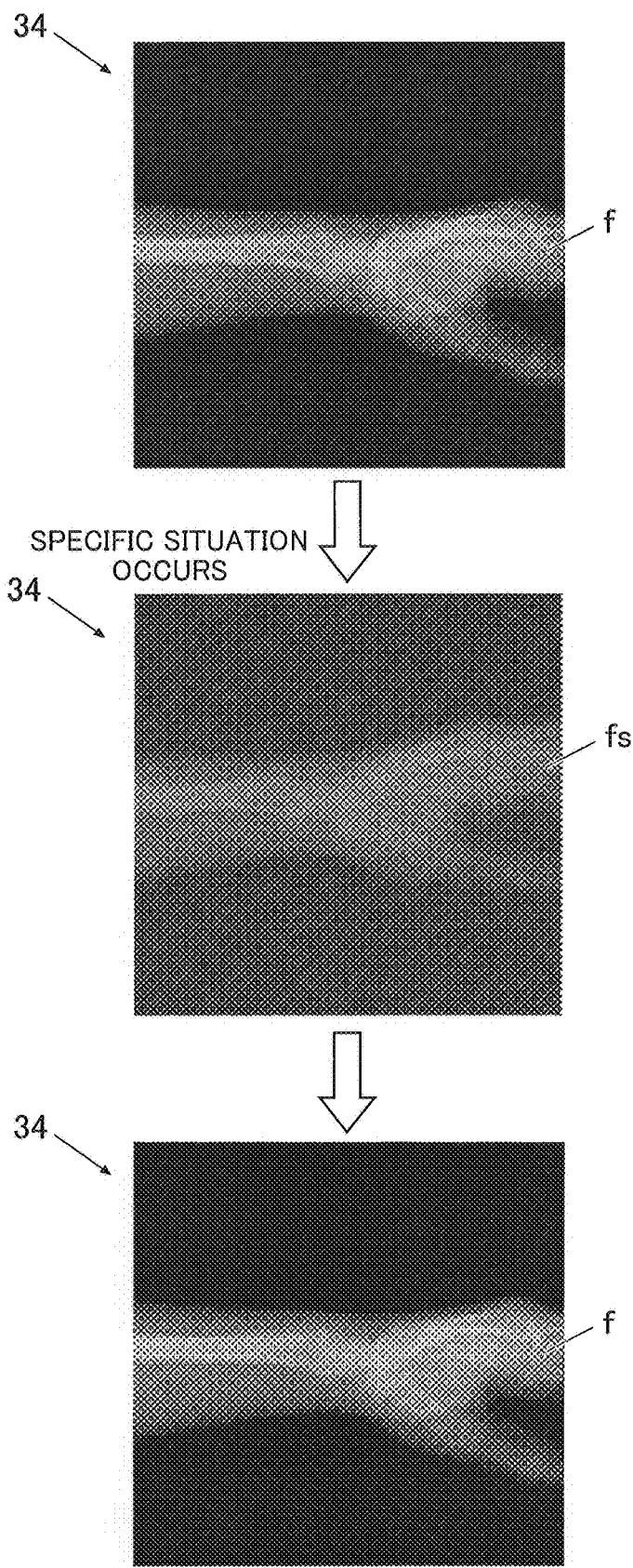
FIG. 5 shows an example of a method of reproducing dynamic images in the radiographic image display apparatus in FIG. 1.

Only the specific frame image fs is displayed with the color being changed (see FIG. 5).

The image is swung only when the specific frame image fs is displayed.

The image is blinked only when the specific frame image fs is displayed.

The display apparatus 3 may include a speaker, and may output a voice (subject's voice) collected by a microphone during occurrence of the specific situation, when displaying the specific frame image fs, or may continuously output the voice collected by the microphone during taking corresponding frame images, while displaying frame images f including the specific frame image fs as dynamic images.

Figure 6:
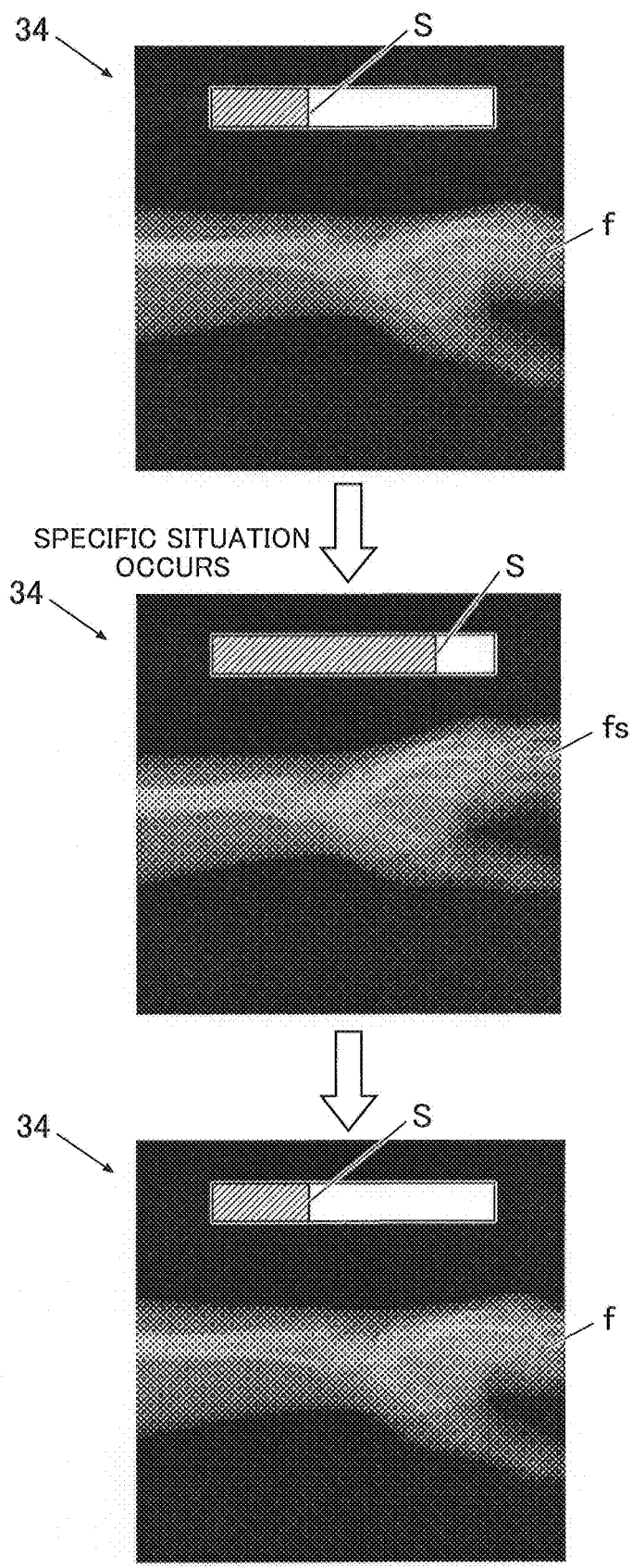
FIG. 6 shows another example of the method of reproducing dynamic images in the radiographic image display apparatus in FIG. 1.

When the intensity of an input from the situation detector 35 is also detected, a scale S (a bar chart, a pie chart, etc.) may be continuously displayed during reproduction of the dynamic images as shown in FIG. 6, for example. Alternatively, the display level may be changed according to the numerical value associated with the frame image, or the loudness may be changed according to the strength of the pain.

(Static Display)

The method of static display may be as follows.

Only the image data on the specific frame image fs is automatically extracted, and only the specific frame image fs is displayed from the beginning.

From the first frame image, the images are sequentially reproduced as normal dynamic images, and the reproduction is stopped at the specific frame image fs as a still image.

[Flows of Imaging and Reading]

Next, the flows of dynamic imaging using the imaging system 100, and reading the dynamic images generated by the imaging system are described.

In the following description, an imaging object site is not specifically designated. However, the present invention is applicable to the movable parts of the entire body (in particular, four extremities are estimated to be effective; likewise, the chest is also believed to be effective).

First, the subject is disposed between the irradiation apparatus 1 and the imaging apparatus 2. The situation detector 35 is brought into a state of allowing an input from the subject to be accepted (the microphone is disposed adjacent, a button is provided, imaging is started by a camera and the like).

Subsequently, when the specific situation occurs during dynamic imaging (feeling pains and sufferings), the user notifies the subject about an instruction of input to the situation detector 35 (outputting a voice, pressing a button, moving the body and the like) and presses the exposure switch 12, thereby starting dynamic imaging. That is, the irradiation apparatus 1 starts irradiation with pulse radiation, and the imaging apparatus 2 starts to generate image data and transmits the pulse signal to the display apparatus.

It is preferred that for dynamic imaging, at least any of the following measures be further taken.

In dynamic imaging after detection of the specific situation, the method of imaging the imaging object site is changed (change to high definition, high radiation dose, high frame rate and the like).

The range of motion is considered, and a wide range is preliminarily selected and imaged so as not to make the imaging object site invisible.

The imaging object site is limited only to a joint and is imaged (to reduce the radiation dose).

A plane formed at the site where the specific situation occurs is irradiated with radiation so as to be orthogonal with this plane centered at the point where the specific situation occurs, and imaging is performed.

The imaging object site is imaged while this site being moved at a cycle in conformity with the imaging object site (using a metronome or the like, for example).

Imaging is performed while a weight is applied.

Accordingly, the diagnostic performance can be improved.

In particular, in the case where the imaging object site is imaged while this site is moved, it is preferred that at least any of the following measures be further taken for the cycle.

An upper limit cycle is defined for the moving cycle.

A lower limit cycle is defined.

Both the upper limit cycle and the lower limit cycle are defined.

At least any of the upper limit cycle and the lower limit cycle, which are to be defined in conformity with the imaging site, is changed.

For example, there is data indicating that a pace of a person is 66 cm for a young group, 64 cm for a young-old group, and 44 cm for an old-old group. In a case where walking at 4 km per hour is assumed, the cycle of moving a knee joint is about 1.2 sec. for the young group, 1.1 sec. for the young-old group, and 0.9 sec. for the old-old group.

Accordingly, in the case where a knee joint is adopted as the imaging object site, it is preferred that the upper limit of the motion cycle be 2.4 sec. (twice that for the young group) and the lower limit be 1.2 sec. (one time that for the young group).

In a case where a cervical spine is adopted as the imaging object site, it is preferred that the upper limit of the motion cycle be 4.8 sec. (four times that of the knee joint for the young group) and the lower limit be 3.6 sec. (three times that of the knee joint for the young group).

In a case where a site other than the knee joint or cervical spine is adopted as the imaging object site, it is preferred that the upper limit of the motion cycle be 3.6 sec. (three times that of the knee joint for the young group) and the lower limit be 2.4 sec. (twice that of the knee joint for the young group).

The upper limit and the lower limit of the cycle defined for each age group may further be corrected in conformity with the ages. For example, the cycle for 60 years old or higher is defined as the cycle=1+(age−60)×0.01.

When the subject comes into the specific situation during repetition of irradiation with pulse radiation and generation of image data, the subject makes a predetermined input to the situation detector 35 according to an instruction having preliminarily been received. Then at the display apparatus 3, the frame number of the dynamic image being taken is associated with the fact that the predetermined input has been made.

The dynamic imaging is completed, and a person in charge of diagnosis (a doctor or the like) causes the obtained dynamic images to be displayed on the display 34 of the display apparatus 3. Subsequently, when the specific frame image fs taken with the subject having come into the specific situation is displayed, the specific output is performed (the color is changed, the screen is swung or blinked, a sound is output, the scale level is increased, the display is switched to the static display or the like).

Accordingly, the reading operator can know that the situation comes into the specific situation when the imaging object site is in a state of being represented in the specific frame image fs. As a result, the reading operator can focus on and read the specific frame image fs and frame images before and after this image, and correctly identify the cause of the specific situation.

As described above, the display apparatus 3 included in the imaging system 100 according to this embodiment includes a hardware processor that obtains an image data item on each of the frame images f generated by the imaging apparatus 2 by performing dynamic imaging, causes a display to display the frame images f based on the obtained image data items, detects a situation of the subject at least at a time point in the dynamic imaging, associates the detected situation of the subject with the obtained image data items, and issues a specific output for notification that the subject is in the specific situation when the subject is in a state of a specific frame image fs, in a case where the display is caused to display the specific frame image fs, this specific frame image fs being taken when it is detected that the situation of the subject is the specific situation.

Accordingly, the reading operator who reads dynamic images obtained by this imaging system 100 can know that the subject is in the specific situation when the imaging object site of the subject is in the state of the specific frame image fs. That is, the timing when the subject comes into the specific situation can be easily and correctly read from the taken dynamic images.

In the case where the imaging object site is the cervical spine, the first and second cervical vertebrae have atlantoaxial structures, and it is known that dislocation sometimes occurs. Only with conventional two still images of bending forward and rearward, it has been difficult to find the dislocation state (specific situation). Also in a case of a knee of a prosthetic joint or the like, it has been difficult to find occurrence of the specific situation only with the two still images of bending and stretching.

However, such sites are dynamically imaged by the imaging system 100 according to this embodiment, and the obtained dynamic images are read, thereby allowing even a specific situation of such sites to be easily found.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-071246, filed on 3 Apr. 2018, is incorporated herein by reference in its entirety.

What is claimed is:

1. A radiographic image display apparatus comprising a hardware processor that:
   obtains an image data item on each of frame images by performing dynamic imaging that repetitively generates a frame image of a subject, the frame images being generated by a radiographic imaging apparatus;
   causes a display to display the frame images based on the obtained image data items;
   detects a situation of the subject at least at a time point in the dynamic imaging;
   associates the detected situation of the subject with the obtained image data items; and
   issues a specific output for notifying that the subject is in a specific situation, the specific situation being a situation in which the subject experiences pain or discomfort, and the specific situation being associated with a specific frame image from among the frame images, the specific output being issued in a case where the display is caused to display the specific frame image, and the specific frame image being taken when it is detected that the situation of the subject is the specific situation.

2. The radiographic image display apparatus according to claim 1, wherein:
   the hardware processor detects the specific situation through a specific input by the subject in the specific situation, and
   a timing when the subject is detected to be in the specific situation is corrected so as to approach a timing when the subject actually comes into the specific situation, based on a table representing a relationship between (i) at least one of attributes including an age and a gender, and (ii) an average amount of delay from occurrence of the specific situation to the specific input.

3. The radiographic image display apparatus according to claim 1, wherein the hardware processor:
   detects a reflexive motion by the subject in the specific situation,
   detects the specific situation through a specific input by the subject in the specific situation, and
   measures a time period from detection of the reflexive motion to the specific input, and corrects a timing when the subject is detected to be in the specific situation so as to approach a timing when the subject actually comes into the specific situation, based on the measured time period.

4. The radiographic image display apparatus according to claim 1, wherein the hardware processor generates diagnosis support information based on the detected specific situation, and causes the display to display the diagnosis support information together with the specific frame image.

5. The radiographic image display apparatus according to claim 1, wherein the hardware processor causes the display to statically display the specific frame image.

6. A radiographic imaging system, comprising:
   a radiation irradiation apparatus that repetitively generates pulse radiation at a predetermined cycle;
   a radiographic imaging apparatus that repetitively generates image data on a radiographic image according to received radiation at a predetermined cycle; and
   the radiographic image display apparatus according to claim 1.

7. A diagnostic method, comprising:
   dynamically imaging a joint or a cervical spine of a subject reciprocatively moving at a certain cycle, using a radiation irradiation apparatus that repetitively generates pulse radiation at a predetermined cycle, and a radiographic imaging apparatus that repetitively generates image data on a frame image according to the received radiation at a predetermined cycle;
   transmitting image data items on obtained frame images to a radiographic image display apparatus that comprises a hardware processor that obtains an image data item on each of frame images generated by the radiographic imaging apparatus, causes a display to display the frame images based on the obtained image data items, detects a situation of the subject at least at a time point in the dynamic imaging, associates the detected situation of the subject with the obtained image data items, and issues a specific output for notifying that the subject is in a specific situation, the specific situation being a situation in which the subject experiences pain or discomfort, and the specific situation being associated with a specific frame image from among the frame images, the specific output being issued in a case where the display is caused to display the specific frame image, and the specific frame image being taken when the subject is detected to be in the specific situation; and
   reading the specific frame image displayed by the display.

8. The radiographic image display apparatus according to claim 1, wherein the hardware processor detects the specific situation through a specific input by the subject in the specific situation.

9. The radiographic image display apparatus according to claim 8, wherein information regarding an intensity of the pain or discomfort is detected based on the specific input.

10. The radiographic image display apparatus according to claim 8, wherein the specific input is received from the subject by at least one of a microphone which collects a voice output by the subject, a push button which is operated by the subject, and a camera that captures an image the subject.

11. The radiographic image display apparatus according to claim 10, wherein information regarding an intensity of the pain or discomfort is detected based on the specific input.

12. The radiographic image display apparatus according to claim 11, wherein the hardware processor detects the information regarding the intensity based on at least one of a loudness of the voice output by the subject, a strength with which the subject operates the push button, and a change in an expression or an attitude of the subject in the image of the subject captured by the camera.

13. A non-transitory computer-readable storage medium having a program stored thereon, the program being executable by a computer to control the computer to execute processes comprising:
   obtaining an image data item on each of frame images by performing dynamic imaging that repetitively generates a frame image of a subject, the frame images being generated by a radiographic imaging apparatus;
   causing a display to display the frame images based on the obtained image data items;
   detecting a situation of the subject at least at a time point in the dynamic imaging;
   associating the detected situation of the subject with the obtained image data items; and
   issuing a specific output for notifying that the subject is in a specific situation, the specific situation being a situation in which the subject experiences pain or discomfort, and the specific situation being associated with a specific frame image from among the frame images, the specific output being issued in a case where the display is caused to display the specific frame image, and the specific frame image being taken when it is detected that the situation of the subject is the specific situation.

\* \* \* \* \*